United States Patent
Ignatyev et al.

(10) Patent No.: US 7,692,007 B2
(45) Date of Patent: Apr. 6, 2010

(54) PROCESS FOR THE PREPARATION OF ONIUM SALTS HAVING A LOW CHLORIDE CONTENT

(75) Inventors: Nikolai (Mykola) Ignatyev, Duisburg (DE); Urs Welz-Biermann, Heppenheim (DE); Peter Barthen, Rheinberg (DE); Helge Willner, Muelheim/Ruhr (DE)

(73) Assignee: Merck Patent Gesellschaft mit beschrankter Haftung, Darmstadt (DE)

( * ) Notice: Subject to any disclaimer, the term of this patent is extended or adjusted under 35 U.S.C. 154(b) by 168 days.

(21) Appl. No.: 11/632,313

(22) PCT Filed: Jun. 17, 2005

(86) PCT No.: PCT/EP2005/006550

§ 371 (c)(1), (2), (4) Date: Jan. 12, 2007

(87) PCT Pub. No.: WO2006/007912

PCT Pub. Date: Jan. 26, 2006

(65) Prior Publication Data

US 2008/0027230 A1  Jan. 31, 2008

(30) Foreign Application Priority Data

Jul. 16, 2004 (DE) ........................ 10 2004 034 543

(51) Int. Cl.
C07D 239/00 (2006.01)
C07D 233/00 (2006.01)
C07D 211/92 (2006.01)
C07F 5/02 (2006.01)

(52) U.S. Cl. ................... 544/242; 548/335.1; 562/807; 562/806; 546/347

(58) Field of Classification Search ................ 546/347; 548/335.1; 562/807, 806; 544/242
See application file for complete search history.

(56) References Cited

U.S. PATENT DOCUMENTS 7,094,328 B2 8/2006 Ignatyev et al.

FOREIGN PATENT DOCUMENTS

WO    WO 00/16902 A  *  3/2000
WO    WO 03/002579 A    1/2003

OTHER PUBLICATIONS

Nishida T. et al., "Physical and electrochemical properties of 1-alkyl-3-methylimidazolium tetrafluoroborate for electrolyte." Journal of Fluorine Chemistry; 120, 2, Apr. 1, 2003, pp. 135-141.

Holbrey JD et al., "The phase behaviour of 1-alkyl-3-methylimidazolium terafluoroborates; ionic liquids and ionic liquid crystals," Journal of the Chemical Society, Section A: Inorganic, Physical and Theoretical Chemistry; No. 13, Jul. 1999, pp. 2133-2139.

Davis, James et al., "Synthesis and purification of Ionic liquids" 2003, Ionic Liquids in Synthesis, 7-21.

* cited by examiner

*Primary Examiner*—Janet L Andres
*Assistant Examiner*—Binta M Robinson
(74) *Attorney, Agent, or Firm*—Millen, White, Zelano, Branigan, P.C.

(57) ABSTRACT

The invention relates to a process for the preparation of onium salts having a low chloride content by reaction of an onium chloride with an acid, where the hydrochloric acid forming is removed by azeotropic distillation by coordination to an organic solvent which forms an azeotropic mixture with water.

32 Claims, No Drawings

PROCESS FOR THE PREPARATION OF ONIUM SALTS HAVING A LOW CHLORIDE CONTENT

The invention relates to a process for the preparation of onium salts by reaction of an onium halide with an acid, where the hydrohalic acid forming is, in accordance with the invention, removed by coordination to an organic solvent which forms an azeotropic mixture with water.

A large number of onium salts are ionic liquids. Due to their properties, ionic liquids represent an effective alternative to traditional volatile organic solvents for organic synthesis in modern research. The use of ionic liquids as novel reaction medium could furthermore be a practical solution both for solvents emission and also for problems in the reprocessing of catalysts.

Review articles on ionic liquids are, for example, R. Sheldon "Catalytic reactions in ionic liquids", *Chem. Commun.*, 2001, 2399-2407; M. J. Earle, K. R. Seddon "Ionic liquids. Green solvent for the future", *Pure Appl. Chem.*, 72 (2000), 1391-1398; P. Wasserscheid, W. Keim "Ionische Flüssigkeiten-neue Lösungen für die Übergangsmetallkatalyse" [ionic Liquids—Novel Solutions for Transition-Metal Catalysis], *Angew. Chem.*, 112 (2000), 3926-3945; T. Welton "Room temperature ionic liquids. Solvents for synthesis and catalysis", *Chem. Rev.*, 92 (1999), 2071-2083 or R. Hagiwara, Ya. Ito "Room temperature ionic liquids of alkylimidazolium cations and fluoroanions", *J. Fluorine Chem.*, 105 (2000), 221-227).

Ionic liquids or liquid salts are ionic species which consist of an organic cation and a generally inorganic anion. They do not contain any neutral molecules and usually have melting points below 373 K. However, the melting point may also be higher without restricting the usability of the salts in all areas of application. Examples of organic cations are, inter alia, tetraalkylammonium, tetraalkylphosphonium, N-alkylpyridinium, 1,3-dialkyl-imidazolium or trialkylsulfonium. Amongst a multiplicity of suitable anions, mention may be made, for example, of $BF_4^-$, $PF_6^-$, $SbF_6^-$, $NO_3^-$, $CF_3SO_3^-$, $(CF_3SO_2)_2N^-$, $arylSO_3^-$, $CF_3CO_2^-$, $CH_3CO_2^-$ or $Al_2Cl_7^-$.

The properties of ionic liquids, for example the melting point, the thermal and electrochemical stability or the viscosity, are determined by the choice of the cations and anions. Ionic liquids are non-volatile materials and therefore cannot be purified by conventional purification methods, such as, for example, distillation, as developed for most organic solvents. In processes for the preparation of onium salts, in particular ionic liquids, the technology is therefore of crucial importance in order that they can be synthesised with low impurity levels through the reaction per se or the way the reaction is carried out. An impurity which is predominantly present in known ionic liquids are halide ions. If the proportion of halide ions, for example chloride ions, is greater than 1000 ppm (0.1%), the usability of the ionic liquid is reduced, in particular in use for electrochemical processes.

The object of the present invention was accordingly to provide an alternative process for the preparation of onium salts having a low chloride content which results in products of high purity in good yield and is also suitable for large-scale industrial production.

The object is achieved by the process according to the invention.

The process according to the invention is an improvement of the known synthetic processes, which are generally 2-step processes, as described in P. Wasserscheid and W. Keim, Angew. Chem. 112 (2000), 3926-3945. In the first step of the known processes, an organic base, typically an amine, phosphine or a heterocyclic compound, is alkylated using an alkyl halide, and the halide forming is, in the second step, converted into the desired salt via anion exchange.

Typically, ionic liquids having the tetrafluoroborate anion are prepared in this way, where the halide, for example 1-ethyl-3-methylimidazolium chloride or bromide, can be reacted in the second step with $NaBF_4$ in acetone by the method of S. Park and R. J. Kazlauskas, J. Organic Chemistry, 66 (2001), 8395-8401, with $NaBF_4$ in water by the method of R. Karmakar and A. Samanta, J. Phys. Chem. A, 106 (2002), 6670-6675, with $AgBF_4$ or $HBF_4$ in water by the method of J. D. Holbrey and K. R. Seddon, J. Chem. Soc., Dalton Trans., (1999), 2133-2139, with $NH_4BF_4$ in acetone by the method of J. Fuller et al, J. Electrochem. Soc., 144 (1997), 3881-3885, with $HBF_4$ in methanol by the method of T. Nishida et al, J. of Fluorine Chem., 120 (2003), 135-141 or with $NH_4BF_4$ with microwave irradiation by the method of V. V. Namboodiri and R. S. Varma, Tetrahedron Lett., 43 (2002), 5381-5383.

All known processes have a disadvantage, in particular for large-scale industrial synthesis, which can be illustrated by the example of the synthesis of ionic liquids having tetrafluoroborate anions. Silver tetrafluoroborate is, for example, an expensive reagent. The reactions with $NaBF_4$, $NH_4BF_4$ and $HBF_4$ in water require a purification step, possibly through the use of $AgBF_4$ or adsorbents. $HBF_4$ in methanol is not commercially available and is more expensive than aqueous $HBF_4$, which is in turn commercially available.

The reaction medium of choice, with respect to large-scale industrial synthesis of onium salts which are water-soluble or partially water-soluble, are water-soluble acids, for example $HBF_4$, $H_2SiF_6$, $H_2TiF_6$, $H_2ZrF_6$, $HSbF_6$, $HAsF_6$, $HPF_6$, $HN(CN)_2$, $HC(CN)_3$, $H_2SO_4$, $HNO_3$, alkyl- or perfluoroalkyl-sulfonic acids, aromatic sulfonic acids, perfluoroalkylcarboxylic acids, alkyl- or perfluoroalkylphosphinic acids, alkyl- or perfluoroalkylphosphonic acids, aromatic phosphinic or phosphonic acids or phosphoric acid. However, there is a general problem in the said reaction, which is advantageously carried out in water or also in water-miscible solvents, since the hydrohalic acid which forms cannot be removed completely by distillation. On removal of the solvent, an equilibrium between two salts and two acids always forms. The onium salts obtained inevitably still contain a few percent of halide ions, documented by investigations by N. M. M Mateus et al, Green Chemistry, 5 (2003), 347-352.

Surprisingly, a simple process has been developed. After reaction of an onium halide with an acid, as described above as the second step of the known reactions, the hydrohalic acid forming can, in accordance with the invention, be removed by azeotropic distillation by coordination to an organic solvent which forms an azeotropic mixture with water. The azeoropic distillation shifts the above-described equilibrium, giving, after multiple distillation if the reaction is carried out batchwise or semicontinuously or by continuous distillation if the reaction is carried out continuously, ionic liquids whose halide content can be below 5000 ppm (=0.5%), preferably below 500 ppm, particularly preferably below 100 ppm, very particularly preferably below 20 ppm.

Organic solvents which are able to form an azeotropic mixture with water are, for example, nitroalkanes, nitriles, aromatics, cyclic or linear ethers or esters or alcohols. Without restricting generality, examples of these solvents are 1,4-dioxane, ethanol, propanol, isopropanol, butanol, nitromethane, acetonitrile, dimethoxyethane, tetrahydrofuran, isobutyronitrile, cyclohexanone, benzene or toluene. Particularly suitable for large-scale industrial synthesis is the use of 1,4-dioxane or isopropanol. Very particularly suitable is the use of 1,4-dioxane.

The process according to the invention can be used for the preparation of onium salts whose cation denotes, for example, ammonium, phosphonium, thiouronium, guanidinium or a heterocyclic cation and whose anion is the anion of the corresponding acid.

Suitable acids are, as described above, $HBF_4$, $H_2SiF_6$, $H_2TiF_6$, $H_2ZrF_6$, $HSbF_6$, $HAsF_6$, $HPF_6$, $HN(CN)_2$, $HC(CN)_3$, $H_2SO_4$, $HNO_3$, alkyl- or perfluoroalkylsulfonic acids, aromatic sulfonic acids, perfluoroalkylcarboxylic acids, alkyl- or perfluoroalkylphosphinic acids, alkyl- or perfluoroalkylphosphonic acids, aromatic phosphinic or phosphonic acids or phosphoric acid. The process according to the invention is particularly suitable for the reaction with aqueous $HBF_4$, $H_2SiF_6$, $H_2TiF_6$, $H_2SO_4$, $CF_3SO_3H$, $CF_3COOH$, toluenesulfonic acid monohydrate or $CH_3SO_3H$. As selection from the particularly suitable group of acids, preference is in turn given to the reaction with aqueous $HBF_4$, $H_2SO_4$, $CF_3SO_3H$, $H_2SiF_6$ or $H_2TiF_6$. The process according to the invention is very particularly suitable for the reaction with $HBF_4$ in water.

Anions of the onium salts are accordingly $[BF_4]^-$, $[SiF_6]^{2-}$, $[TiF_6]^{2-}$, $[SbF_6]^-$, $[AsF_6]^-$, $[PF_6]^-$, $[N(CN)_2]^-$, $[C(CN)_3]^-$, $[HSO_4]^-$, $[NO_3]^-$, alkyl- or perfluoroalkyl-sulfonate, for example $[CH_3SO_3]^-$, $[C_2H_5SO_3]^-$, $[CF_3SO_3]^-$, $[C_2F_5SO_3]^-$, anions of aromatic sulfonic acids, for example tosylate, mesylate or phenylsulfonate, perfluoroalkylcarboxylates, for example $[CF_3CO_2]^-$ or $[C_2F_5CO_2]^-$, anions of alkyl- or perfluoroalkylphosphinic acids, for example $(CH_3)_2P(O)O^-$, $(C_2H_5)_2P(O)O^-$, $(C_3H_7)_2P(O)O^-$, $(C_4H_9)_2P(O)O^-$, $(C_2F_5)_2P(O)O^-$, $(C_3F_7)_2P(O)O^-$, $(C_4F_9)_2P(O)O^-$, anions of alkyl- or perfluoroalkylphosphonic acids, for example $[(C_2F_5)P(O)O_2]^{2-}$, $[(C_3F_7)P(O)O_2]^{2-}$, $[(C_4F_9)P(O)O_2]^{2-}$, anions of aromatic phosphinic or phosphonic acids, for example $(C_6H_5)_2P(O)O^-$, or phosphates.

Suitable onium halides are ammonium halides, phosphonium halides, thiouronium halides, guanidinium halides or halides having a heterocyclic cation, where the halides can be selected from the group of chlorides or bromides. Chlorides are particularly suitable.

Ammonium chlorides can be described, for example, by the formula (1)

phosphonium chlorides can be described, for example, by the formula (2)

where
R in each case, independently of one another, denotes
H, where all substituents R cannot simultaneously be H,
straight-chain or branched alkyl having 1-20 C atoms,
straight-chain or branched alkenyl having 2-20 C atoms and one or more double bonds,
straight-chain or branched alkynyl having 2-20 C atoms and one or more triple bonds,
saturated, partially or fully unsaturated cycloalkyl having 3-7 C atoms, which may be substituted by alkyl groups having 1-6 C atoms,
where one or more R may be partially or fully substituted by halogens, in particular —F and/or —Cl, or partially by —$NO_2$,
and where, in the R, one or two non-adjacent carbon atoms which are not in the α-position may be replaced by atoms and/or atom groups selected from the group —O—, —S—, —S(O)—, —$SO_2$— or —P(O)R'—, where R'=non-, partially or perfluorinated $C_1$- to $C_6$-alkyl, $C_3$- to $C_7$-cycloalkyl, unsubstituted or substituted phenyl.

However, compounds of the formulae (1) and (2) in which all four or three substituents R are fully substituted by halogens, for example tris(trifluoromethyl)methylammonium chloride, tetra(trifluoromethyl)ammonium chloride or tetra (nonafluorobutyl)ammonium chloride, are excluded.

Thiouronium chlorides can be described by the formula (3)

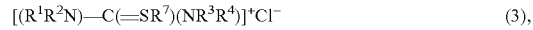

guanidinium chlorides by the formula (4)

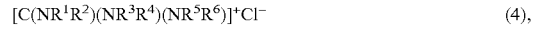

where
$R^1$ to $R^7$ each, independently of one another, denote hydrogen, where hydrogen is excluded for $R^7$,
straight-chain or branched alkyl having 1 to 20 C atoms,
straight-chain or branched alkenyl having 2-20 C atoms and one or more double bonds,
straight-chain or branched alkynyl having 2-20 C atoms and one or more triple bonds,
saturated, partially or fully unsaturated cycloalkyl having 3-7 C atoms, which may be substituted by alkyl groups having 1-6 C atoms,
where one or more of the substituents $R^1$ to $R^7$ may be partially or fully substituted by halogens, in particular —F and/or —Cl, or partially by —$NO_2$, but where all substituents on an N atom cannot be fully substituted by halogens,
and where, in the substituents $R^1$ to $R^6$, one or two non-adjacent carbon atoms which are not bonded directly to the heteroatom may be replaced by atoms and/or atom groups selected from the group —O—, —S—, —S(O)—, —$SO_2$— or —P(O)R'—, where R'=non-, partially or perfluorinated $C_1$- to $C_6$-alkyl, $C_3$- to $C_7$-cycloalkyl, unsubstituted or substituted phenyl.

Chlorides having a heterocyclic cation can be described, for example, by the formula (6)

where
HetN$^+$ denotes a heterocyclic cation selected from the group

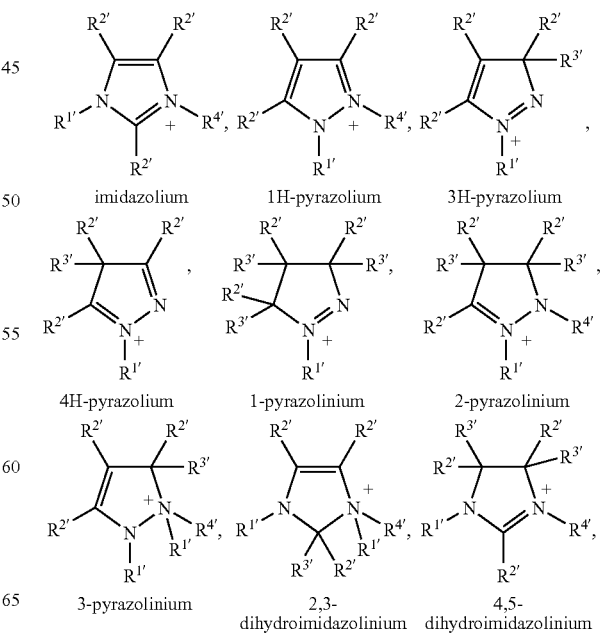

imidazolium    1H-pyrazolium    3H-pyrazolium 4H-pyrazolium    1-pyrazolinium    2-pyrazolinium 3-pyrazolinium    2,3-dihydroimidazolinium    4,5-dihydroimidazolinium -continued

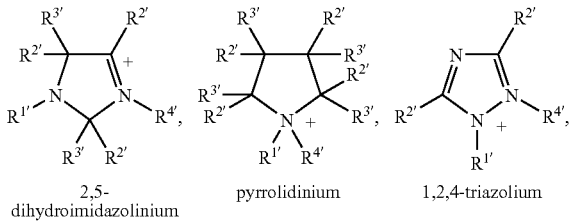

2,5-dihydroimidazolinium    pyrrolidinium    1,2,4-triazolium

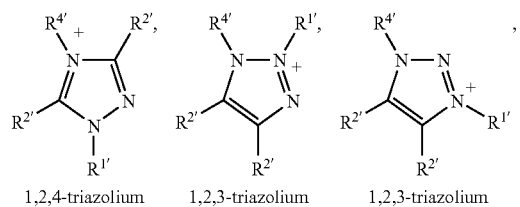

1,2,4-triazolium    1,2,3-triazolium    1,2,3-triazolium

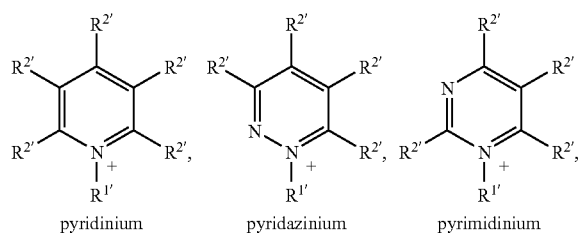

pyridinium    pyridazinium    pyrimidinium

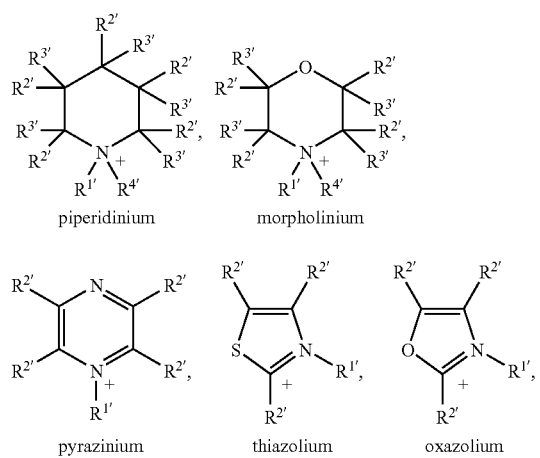

piperidinium    morpholinium pyrazinium    thiazolium    oxazolium

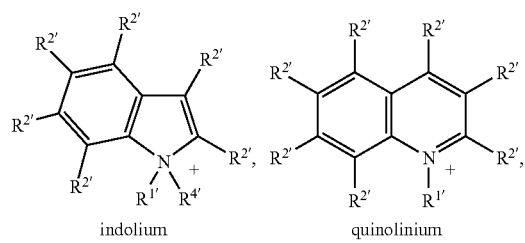

indolium    quinolinium

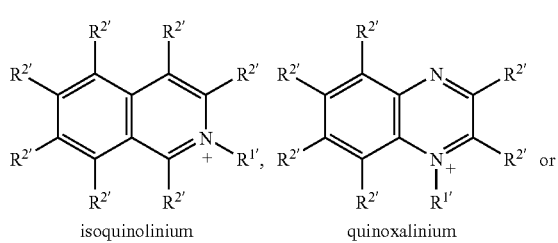

isoquinolinium    quinoxalinium

-continued

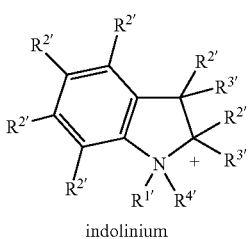

indolinium where the substituents $R^{1'}$ to $R^{4'}$ each, independently of one another, denote hydrogen, straight-chain or branched alkyl having 1-20 C atoms, straight-chain or branched alkenyl having 2-20 C atoms and one or more double bonds, straight-chain or branched alkynyl having 2-20 C atoms and one or more triple bonds, saturated, partially or fully unsaturated cycloalkyl having 3-7 C atoms, which may be substituted by alkyl groups having 1-6 C atoms, saturated, partially or fully unsaturated heteroaryl, heteroaryl-$C_1$-$C_6$-alkyl or aryl-$C_1$-$C_6$-alkyl, where the substituents $R^{1'}$, $R^{2'}$, $R^{3'}$ and/or $R^{4'}$ together may also form a ring system, where one or more substituents $R^{1'}$ to $R^{4'}$ may be partially or fully substituted by halogens, in particular —F and/or —Cl, or partially by —NO$_2$, but where $R^{1'}$ and $R^{4'}$ cannot simultaneously be fully substituted by halogens, and where, of the substituents $R^{1'}$ to $R^{4'}$, one or two non-adjacent carbon atoms which are not bonded to the heteroatom may be replaced by atoms and/or atom groups selected from the group —O—, —S—, —S(O)—, —SO$_2$— or —P(O)R'—, where R'=non-, partially or perfluorinated $C_1$- to $C_6$-alkyl, $C_3$- to $C_7$-cycloalkyl, unsubstituted or substituted phenyl.

For the purposes of the present invention, fully unsaturated substituents are also taken to mean aromatic substituents.

Besides hydrogen, suitable substituents R and $R^1$ to $R^7$ of the compounds of the formulae (1) to (5) are preferably, in accordance with the invention: $C_1$- to $C_{20}$-, in particular $C_1$- to $C_{14}$-alkyl groups, and saturated or unsaturated, i.e. also aromatic, $C_3$- to $C_7$-cycloalkyl groups, which may be substituted by $C_1$- to $C_6$-alkyl groups, in particular phenyl.

The substituents R in the compounds of the formula (1) or (2) may be identical or different here. The substituents R are preferably identical.

The substituent R is particularly preferably methyl, ethyl, isopropyl, propyl, butyl, sec-butyl, pentyl, hexyl, octyl, decyl or tetradecyl.

Up to four substituents of the guanidinium cation $[C(NR^1R^2)(NR^3R^4)(NR^5R^6)]^+$ may also be connected in pairs in such a way that mono-, bi- or polycyclic cations are formed.

Without restricting generality, examples of such guanidinium cations are:

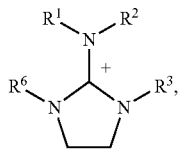 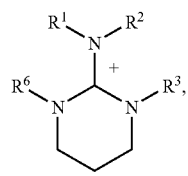

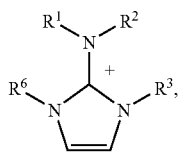 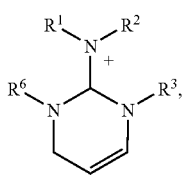

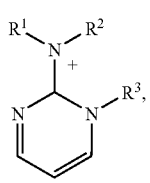 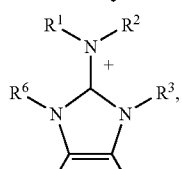

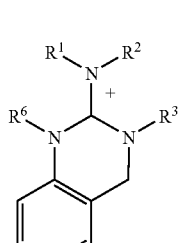 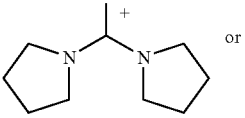 or

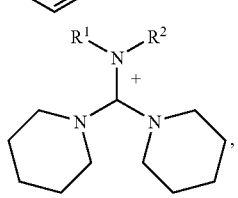

where the substituents $R^1$ to $R^3$ and $R^6$ may have an above-mentioned or particularly preferred meaning.

The carbocycles or heterocycles of the above-mentioned guanidinium cations may optionally also be substituted by $C_1$- to $C_6$-alkyl, $C_1$- to $C_6$-alkenyl, $NO_2$, F, Cl, Br, I, OH, $C_1$-$C_6$-alkoxy, $SCF_3$, $SO_2CF_3$, COOH, $SO_2NR''_2$, $SO_2X'$ or $SO_3H$, where $X'$ and $R''$ have a meaning indicated above or below, substituted or unsubstituted phenyl or an unsubstituted or substituted heterocycle.

Up to four substituents of the thiouronium cation $[(R^1R^2N)-C(=SR^7)(NR^3R^4)]^+$ may also be connected in pairs in such a way that mono-, bi- or polycyclic cations are formed.

Without restricting generality, examples of such cations are indicated below, where Y=S:

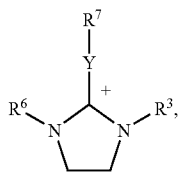 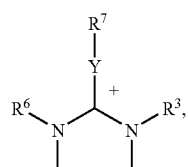

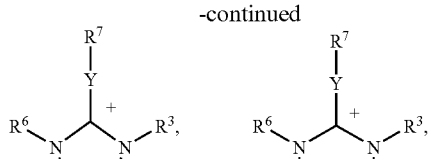

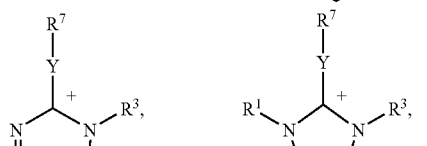

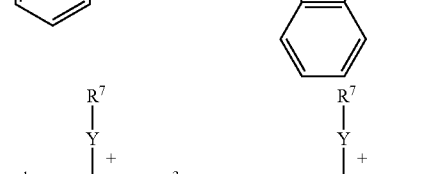 or

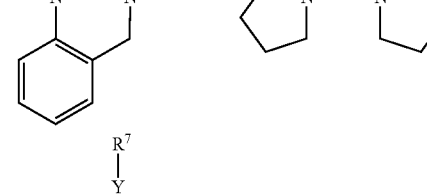

where the substituents $R^1$, $R^3$ and $R^7$ may have an above-mentioned or particularly preferred meaning.

The carbocycles or heterocycles of the above-mentioned cations may optionally also be substituted by $C_1$- to $C_6$-alkyl, $C_1$- to $C_6$-alkenyl, $NO_2$, F, Cl, Br, I, OH, $C_1$-$C_6$-alkoxy, $SCF_3$, $SO_2CF_3$, COOH, $SO_2NR''_2$, $SO_2X'$ or $SO_3H$ or substituted or unsubstituted phenyl or an unsubstituted or substituted heterocycle, where $X'$ and $R''$ have an above-mentioned meaning.

The substituents $R^1$ to $R^7$ are each, independently of one another, preferably a straight-chain or branched alkyl group having 1 to 10 C atoms. The substituents $R^1$ and $R^2$, $R^3$ and $R^4$ and $R^5$ and $R^6$ in compounds of the formulae (3) to (5) may be identical or different here.

$R^1$ to $R^7$ are particularly preferably each, independently of one another, methyl, ethyl, n-propyl, isopropyl, n-butyl, sec-butyl, phenyl or cyclohexyl, very particularly preferably methyl, ethyl, n-propyl, isopropyl or n-butyl.

Besides hydrogen, suitable substituents $R^{1'}$ to $R^{4'}$ of compounds of the formula (6) are preferably, in accordance with the invention: $C_1$- to $C_{20}$-, in particular $C_1$- to $C_{12}$-alkyl groups, and saturated or unsaturated, i.e. also aromatic, $C_3$- to $C_7$-cycloalkyl groups, which may be substituted by $C_1$- to $C_6$-alkyl groups, in particular phenyl.

The substituents $R^{1'}$ and $R^{4'}$ are each, independently of one another, particularly preferably methyl, ethyl, isopropyl, propyl, butyl, sec-butyl, pentyl, hexyl, octyl, decyl, cyclohexyl, phenyl or benzyl. They are very particularly preferably methyl, ethyl, n-butyl or hexyl. In pyrrolidinium, piperidinium or indolinium compounds, the two substituents $R^{1'}$ and $R^{4'}$ are preferably different.

The substituent $R^{2'}$ or $R^{3'}$ is in each case, independently of one another, in particular, hydrogen, methyl, ethyl, isopropyl, propyl, butyl, sec-butyl, cyclohexyl, phenyl or benzyl. $R^{2'}$ is particularly preferably hydrogen, methyl, ethyl, isopropyl, propyl, butyl or sec-butyl. $R^{2'}$ and $R^{3'}$ are very particularly preferably hydrogen.

The $C_1$-$C_{12}$-alkyl group is, for example, methyl, ethyl, isopropyl, propyl, butyl, sec-butyl or tert-butyl, furthermore also pentyl, 1-, 2- or 3-methylbutyl, 1,1-, 1,2- or 2,2-dimethylpropyl, 1-ethylpropyl, hexyl, heptyl, octyl, nonyl, decyl, undecyl or dodecyl. Optionally difluoromethyl, trifluoromethyl, pentafluoroethyl, heptafluoropropyl or nonafluorobutyl.

A straight-chain or branched alkenyl having 2 to 20 C atoms, where a plurality of double bonds may also be present, is, for example, allyl, 2- or 3-butenyl, isobutenyl, sec-butenyl, furthermore 4-pentenyl, isopentenyl, hexenyl, heptenyl, octenyl, —$C_9H_{17}$, —$C_{10}H_{19}$ to —$C_{20}H_{39}$; preferably allyl, 2- or 3-butenyl, isobutenyl, sec-butenyl, preference is furthermore given to 4-pentenyl, isopentenyl or hexenyl.

A straight-chain or branched alkynyl having 2 to 20 C atoms, where a plurality of triple bonds may also be present, is, for example, ethynyl, 1- or 2-propynyl, 2- or 3-butynyl, furthermore 4-pentynyl, 3-pentynyl, hexynyl, heptynyl, octynyl, —$C_9H_{15}$, —$C_{10}H_{17}$ to —$C_{20}H_{37}$, preferably ethynyl, 1- or 2-propynyl, 2- or 3-butynyl, 4-pentynyl, 3-pentynyl or hexynyl.

Aryl-$C_1$-$C_6$-alkyl denotes, for example, benzyl, phenylethyl, phenylpropyl, phenylbutyl, phenylpentyl or phenylhexyl, where both the phenyl ring and also the alkylene chain may be partially or fully substituted, as described above, by halogens, in particular —F and/or —Cl, or partially by —$NO_2$.

Unsubstituted saturated or partially or fully unsaturated cycloalkyl groups having 3-7 C atoms are therefore cyclopropyl, cyclobutyl, cyclopentyl, cyclohexyl, cycloheptyl, cyclopentenyl, cyclopenta-1,3-dienyl, cyclohexenyl, cyclohexa-1,3-dienyl, cyclohexa-1,4-dienyl, phenyl, cycloheptenyl, cyclohepta-1,3-dienyl, cyclohepta-1,4-dienyl or cyclohepta-1,5-dienyl, which may be substituted by $C_1$- to $C_6$-alkyl groups, where the cycloalkyl group or the cycloalkyl group which is substituted by $C_1$- to $C_6$-alkyl groups may in turn also be substituted by halogen atoms, such as F, Cl, Br or I, in particular F or Cl, or $NO_2$.

In the substituents R, $R^1$ to $R^6$ or $R^{1'}$ to $R^{4'}$, one or two non-adjacent carbon atoms which are not bonded in the α-position to the heteroatom may also be replaced by atoms and/or atom groups selected from the group —O—, —S—, —S(O)—, —$SO_2$— or —P(O)R'—, where R'=non-, partially or perfluorinated $C_1$- to $C_6$-alkyl, $C_3$- to $C_7$-cycloalkyl, unsubstituted or substituted phenyl.

Without restricting generality, examples of substituents R, $R^1$ to $R^6$ and $R^{1'}$ to $R^{4'}$ which have been modified in this way are: —$OCH_3$, —$OCH(CH_3)_2$, —$CH_2OCH_3$, —$CH_2$—$CH_2$—O—$CH_3$, —$C_2H_4OCH(CH_3)_2$, —$C_2H_4SC_2H_5$, —$C_2H_4SCH(CH_3)_2$, —$S(O)CH_3$, —$SO_2CH_3$, —$SO_2C_6H_5$, —$SO_2C_3H_7$, —$SO_2CH(CH_3)_2$, —$SO_2CH_2CF_3$, —$CH_2SO_2CH_3$, —O—$C_4H_8$—O—$C_4H_9$, —$CF_3$, —$C_2F_5$, —$C_3F_7$, —$C_4F_9$, —$C(CF_3)_3$, —$CF_2SO_2CF_3$, —$C_2F_4N(C_2F_5)C_2F_5$, —$CHF_2$, —$CH_2CF_3$, —$C_2F_2H_3$, —$C_3FH_6$, —$CH_2C_3F_7$, —$CH_2C(O)OH$, —$CH_2C_6H_5$, —$C(O)C_6H_5$ or $P(O)(C_2H_5)_2$.

In R', $C_3$- to $C_7$-cycloalkyl is, for example, cyclopropyl, cyclobutyl, cyclopentyl, cyclohexyl or cycloheptyl.

In R', substituted phenyl denotes phenyl which is substituted by $C_1$- to $C_6$-alkyl, $C_1$- to $C_6$-alkenyl, $NO_2$, F, Cl, Br, I, OH, $C_1$-$C_6$-alkoxy, $SCF_3$, $SO_2CF_3$, COOH, $SO_2X'$, $SO_2NR''_2$ or $SO_3H$, where X' denotes F, Cl or Br and R" denotes a non-, partially or perfluorinated $C_1$- to $C_6$-alkyl or $C_3$- to $C_7$-cycloalkyl, as defined for R', for example o-, m- or p-methylphenyl, o-, m- or p-ethylphenyl, o-, m- or p-propylphenyl, o-, m- or p-isopropylphenyl, o-, m- or p-tert-butylphenyl, o-, m- or p-nitrophenyl, o-, m- or p-hydroxyphenyl, o-, m- or p-methoxyphenyl, o-, m- or p-ethoxyphenyl, o-, m-, p-(trifluoromethyl)-phenyl, o-, m-, p-(trifluoromethoxy)phenyl, o-, m-, p-(trifluoromethylsulfonyl)phenyl, o-, m- or p-fluorophenyl, o-, m- or p-chlorophenyl, o-, m- or p-bromophenyl, o-, m- or p-iodophenyl, furthermore preferably 2,3-, 2,4-, 2,5-, 2,6-, 3,4- or 3,5-dimethylphenyl, 2,3-, 2,4-, 2,5-, 2,6-, 3,4- or 3,5-di-hydroxyphenyl, 2,3-, 2,4-, 2,5-, 2,6-, 3,4- or 3,5-difluorophenyl, 2,3-, 2,4-, 2,5-, 2,6-, 3,4- or 3,5-dichlorophenyl, 2,3-, 2,4-, 2,5-, 2,6-, 3,4- or 3,5-di-bromophenyl, 2,3-, 2,4-, 2,5-, 2,6-, 3,4- or 3,5-dimethoxyphenyl, 5-fluoro-2-methylphenyl, 3,4,5-trimethoxyphenyl or 2,4,5-trimethylphenyl.

In $R^{1'}$ to $R^{4'}$, heteroaryl is taken to mean a saturated or unsaturated mono- or bicyclic heterocyclic radical having 5 to 13 ring members, in which 1, 2 or 3 N and/or 1 or 2 S or O atoms may be present and the heterocyclic radical may be mono- or polysubstituted by $C_1$- to $C_6$-alkyl, $C_1$- to $C_6$-alkenyl, $NO_2$, F, Cl, Br, I, OH, $C_1$-$C_6$-alkoxy, $SCF_3$, $SO_2CF_3$, COOH, $SO_2X'$, $SO_2NR''_2$ or $SO_3H$, where X' and R" have an above-mentioned meaning.

The heterocyclic radical is preferably substituted or unsubstituted 2- or 3-furyl, 2- or 3-thienyl, 1-, 2- or 3-pyrrolyl, 1-, 2-, 4- or 5-imidazolyl, 3-, 4- or 5-pyrazolyl, 2-, 4- or 5-oxazolyl, 3-, 4- or 5-isoxazolyl, 2-, 4- or 5-thiazolyl, 3-, 4- or 5-isothiazolyl, 2-, 3- or 4-pyridyl, 2-, 4-, 5- or 6-pyrimidinyl, furthermore preferably 1,2,3-triazol-1-, 4- or -5-yl, 1,2,4-triazol-1-, -4- or -5-yl, 1- or 5-tetrazolyl, 1,2,3-oxadiazol-4- or -5-yl 1,2,4-oxadiazol-3- or -5-yl, 1,3,4-thiadiazol-2- or -5-yl, 1,2,4-thiadiazol-3- or -5-yl, 1,2,3-thiadiazol-4- or -5-yl, 2-, 3-, 4-, 5- or 6-2H-thiopyranyl, 2-, 3- or 44H-thiopyranyl, 3- or 4-pyridazinyl, pyrazinyl, 2-, 3-, 4-, 5-, 6- or 7-benzofuryl, 2-, 3-, 4-, 5-, 6- or 7-benzothienyl, 1-, 2-, 3-, 4-, 5-, 6- or 7-1 H-indolyl, 1-, 2-, 4- or 5-benzimidazolyl, 1-, 3-, 4-, 5-, 6- or 7-benzopyrazolyl, 2-, 4-, 5-, 6- or 7-benzoxazolyl, 3-, 4-, 5-, 6- or 7-benzisoxazolyl, 2-, 4-, 5-, 6- or 7-benzothiazolyl, 2-, 4-, 5-, 6- or 7-benzisothiazolyl, 4-, 5-, 6- or 7-benz-2,1,3-oxadiazolyl, 1-, 2-, 3-, 4-, 5-, 6-, 7- or 8-quinolinyl, 1-, 3-, 4-, 5-, 6-, 7- or 8-isoquinolinyl, 1-, 2-, 3-, 4- or 9-carbazolyl, 1-, 2-, 3-, 4-, 5-, 6-, 7-, 8- or 9-acridinyl, 3-, 4-, 5-, 6-, 7- or 8-cinnolinyl, 2-, 4-, 5-, 6-, 7- or 8-quinazolinyl or 1-, 2- or 3-pyrrolidinyl.

Analogously to aryl-$C_1$-$C_6$-alkyl, heteroaryl-$C_1$-$C_6$-alkyl is taken to mean, for example, pyridinylmethyl, pyridinylethyl, pyridinylpropyl, pyridinylbutyl, pyridinylpentyl, pyridinylhexyl, where the above-described heterocycles may furthermore be linked to the alkylene chain in this manner.

HetN$^+$ is preferably

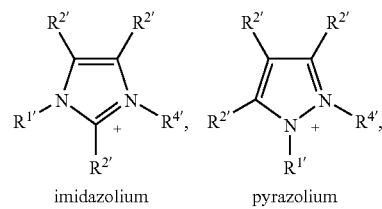

imidazolium    pyrazolium

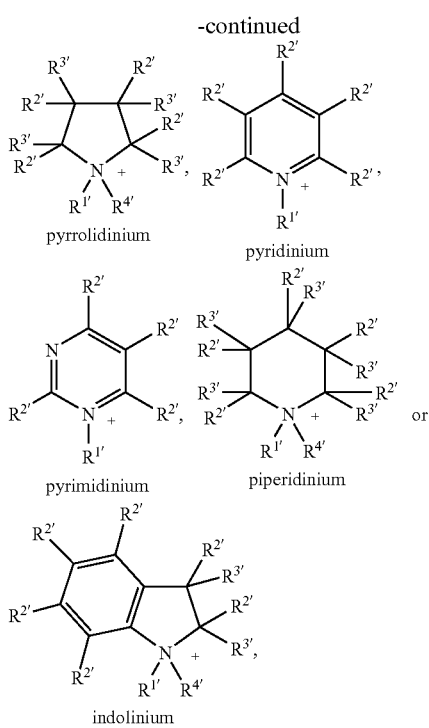

where the substituents $R^{1'}$ to $R^{4'}$ each, independently of one another, have a meaning described above.

HetN$^+$ is particularly preferably imidazolium, pyrrolidinium or pyridinium, as defined above, where the substituents $R^{1'}$ to $R^{4'}$ each, independently of one another, have a meaning described above. HetN$^+$ is very particularly preferably imidazolium, where the substituents $R^{1'}$ to $R^{4'}$ each, independently of one another, have a meaning described above.

A general scheme summarises the process according to the invention, where the arrow in the case of the hydrochloric acid HCl forming represents a symbol for azeotropic distillation:

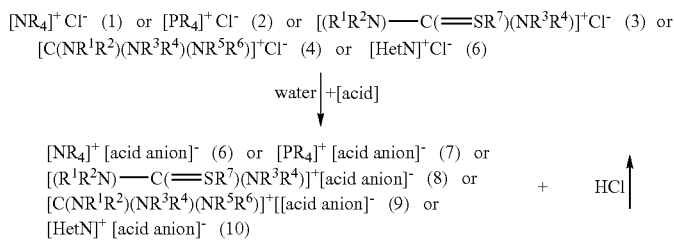

The substituents R, $R^1$ to $R^7$ and HetN$^+$ of the compounds of the formulae (1) to (10) correspond to the meanings as described above.

The anion exchange is carried out under reaction conditions which are known to the person skilled in the art. The solvent used is preferably water. However, it is also possible to employ solvents which are miscible with water, for example dimethoxyethane, acetonitrile, acetone, tetrahydrofuran, dimethylformamide, dimethyl sulfoxide, dioxane, propionitrile, methanol, ethanol or isopropanol, or mixtures with one another or with water.

The reaction can be carried out, for example, at temperatures of 0° C. to 100° C., preferably at 10° to 50° C., particularly preferably at room temperature. The reaction is carried out with an excess or equimolar amount of acid. An excess of 0.1 to 5 mol % of acid is preferably used. The azeotropic distillation is carried out a number of times under atmospheric pressure or under reduced pressure. Under reduced pressure here is taken to mean pressures of 0.1 Pa to atmospheric pressure. The low chloride content is preferably achieved if the azeotropic distillation is carried out five times. The low chloride content is particularly preferably achieved if the azeotropic distillation is carried out three times.

Even without further comments, it is assumed that a person skilled in the art will be able to utilise the above description in the broadest scope. The preferred embodiments and examples should therefore merely be regarded as descriptive disclosure which is absolutely not limiting in any way.

The NMR spectra were measured on solutions in deuterated solvents at 20° C. in a Bruker Avance 300 spectrometer with a 5 mm $^1$H/BB broad-band head with deuterium lock, if not indicated in the examples. The measurement frequencies of the various nuclei are: $^1$H: 300.13 MHz, $^{11}$B: 96.92 MHz, $^{19}$F: 282.41 MHz and $^{31}$P: 121.49 MHz. The referencing method is indicated separately for each spectrum or each data set.

EXAMPLE 1

Synthesis of 1-butyl-3-methylimidazolium tetrafluoroborate

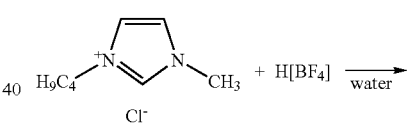

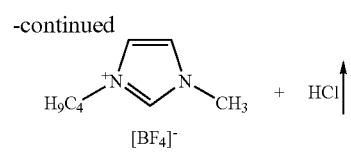

116.5 g (0.667 mol) of 1-butyl-3-methylimidazolium chloride are initially introduced at 70° C. in the liquid state and dissolved in 120.6 g of approx. 50% aqueous HBF$_4$ (approx.

3% excess). No warming and only slight HCl gas formation is observed in the process. 250 ml of 1,4-dioxane are subsequently added, and 250 ml of HCl-containing water/dioxane azeotrope are distilled off at atmospheric pressure (85-90° C.). A further 200 ml of dioxane are then added, and 250 ml of HCl-containing water/dioxane mixture are distilled off at atmospheric pressure (85-101° C.). The residue in the distillation flask has a low content of chloride ions (silver nitrate test). After a further azeotropic distillation with 100 ml of dioxane, the chloride ion content in the residue is too low to be detected using the silver nitrate test. Drying of the distillation residue under reduced pressure at 1.3 Pa and 80° C. gives 149.2 g of 1-butyl-3-methylimidazolium tetrafluoroborate as liquid. The yield of 1-butyl-3-methylimidazolium tetrafluoroborate is approximately quantitative. The chloride content in the ionic liquid is 11 ppm, measured by microtitration using a silver nitrate solution in non-aqueous medium. The end point is determined potentiometrically using a Cl-selective electrode.

$^1$H NMR spectrum, ppm (acetonitrile-D$_3$; reference: TMS): 0.93 t (CH$_3$); 1.32 m (CH$_2$); 1.82 m (CH$_2$); 3.85 s (CH$_3$); 4.16 t (CH$_2$); 7.40 d,d (CH); 7.44 d,d (CH); 8.54 m (CH); $^3J_{H,H}$=7.3 Hz; $J_{H,H}$=1.8 Hz.

$^{11}$B NMR spectrum, ppm (acetonitrile-D$_3$; reference: BF$_3$.OEt$_2$-external): −1.12 s (BF$_4^-$).

$^{19}$F NMR spectrum, ppm (acetonitrile-D$_3$; reference: CCl$_3$F-internal): −149.53 br.s (BF$_4^-$).

EXAMPLE 2

Synthesis of 1-butyl-4-methylpyridinium tetrafluoroborate

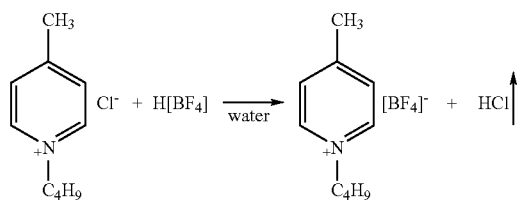

19.5 g of a 50% aqueous solution of HBF$_4$ (0.111 mol) are added to 19.8 g (0.107 mol) of 1-butyl-4-methylpyridinium chloride, and the mixture is stirred at room temperature for 20 min. 20 ml of 1,4-dioxane are then added, and 28 ml of azeotropic 1,4-dioxane/water mixture are distilled off at atmospheric pressure and 85-95° C. The process is repeated until chloride can no longer be detected in the silver nitrate test.

Drying under reduced pressure at 1.3 Pa and 80° C. gives 25.1 g of 1-butyl-4-methylpyridinium tetrafluoroborate, which corresponds to a yield of 99.0%, based on 1-butyl-4-methylpyridinium chloride.

$^1$H NMR spectrum, ppm (acetonitrile-D$_3$; reference: TMS): 0.93 t (CH$_3$); 1.35 m (CH$_2$); 1.93 m (CH$_2$); 2.63 s (CH$_3$); 4.50 t (CH$_2$); 7.86 d (2CH); 8.61 d (2CH); $^3J_{H,H}$=7.4 Hz; $^3J_{H,H}$=6.8 Hz.

$^{11}$B NMR spectrum, ppm (acetonitrile-D$_3$; reference: BF$_3$.OEt$_2$-external): −1.11 s (BF$_4^-$).

$^{19}$F NMR spectrum, ppm (acetonitrile-D$_3$; reference: CCl$_3$F-internal): −149.66 br.s (BF$_4^-$).

EXAMPLE 3

Synthesis of 1-ethyl-3-methylimidazolium tetrafluoroborate

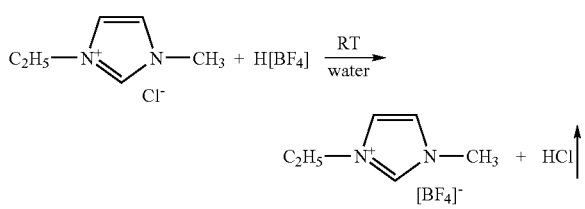

105 g (0.716 mol) of 1-ethyl-3-methylimidazolium chloride are dissolved in 129.5 g of approx. 50% aqueous HBF$_4$ (approx. 3% excess) at RT (room temperature). No warming and only slight HCl gas formation is observed in the process. 260 ml of 1,4-dioxane are subsequently added, and 260 ml of HCl-containing water/dioxane azeotrope are distilled off at atmospheric pressure (85-90° C.). A further 210 ml of dioxane are then added, and 260 ml of HCl-containing water/dioxane mixture are distilled off at atmospheric pressure (85-101° C.). The residue in the distillation flask has a low content of chloride ions (silver nitrate test). After a further azeotropic distillation with 120 ml of dioxane, the chloride ion content in the residue is too low to be detected using the silver nitrate test.

Drying of the distillation residue under reduced pressure at 1.3 Pa and 70° C. gives 1-ethyl-3-methylimidazolium tetrafluoroborate as liquid. The yield is approximately quantitative. The chloride content in the ionic liquid is less than 5 ppm, measured as described in Example 1.

$^1$H NMR spectrum, ppm (acetonitrile-D$_3$; reference: TMS): 1.44 t (CH$_3$); 3.85 s (CH$_3$); 4.18 q (CH$_2$); 7.40 d,d (CH); 7.46 d,d (CH); 8.53 m (CH); $^3J_{H,H}$=7.3 Hz; $J_{H,H}$=1.8 Hz.

$^{19}$F NMR spectrum, ppm (acetonitrile-D$_3$; reference: CCl$_3$F-internal): −149.12 br.s (BF$_4^-$).

EXAMPLE 4

Synthesis of trihexyl(tetradecyl)phosphonium tetrafluoroborate

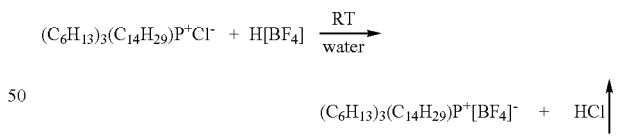

Analogously to Example 1, 54.35 g (0.105 mol) of trihexyl (tetradecyl)phosphonium chloride are reacted with 18.90 g of approx. 50% aqueous HBF$_4$. 40 ml of 1,4-dioxane are subsequently added, and 48 ml of HCl-containing water/dioxane azeotrope are distilled off at atmospheric pressure (85-90° C.). A further 30 ml of dioxane are then added, and 30 ml of HCl-containing water/dioxane mixture are distilled off at atmospheric pressure (85-101° C.). After a further azeotropic distillation with 30 ml of dioxane, the chloride ion content in the residue is too low to be detected using the silver nitrate test.

Drying of the distillation residue under reduced pressure at 1.3 Pa and 70° C. gives trihexyl(tetradecyl)phosphonium tetrafluoroborate as liquid. The yield is approximately quanti-

EXAMPLE 5

Synthesis of tetrabutylammonium tetrafluoroborate

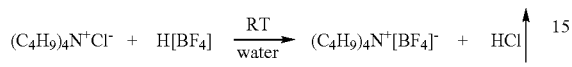

Analogously to Example 1, 24.80 g (0.089 mol) of tetrabutylammonium chloride are reacted with 16.2 g of approx. 50% aqueous $HBF_4$ (approx. 3% excess). After triple addition of 40 ml of 1,4-dioxane and azeotropic distillation of approx. 42 to 45 ml of HCl-containing water/dioxane azeotrope (85-90° C.), the chloride ion content in the residue is low in the silver nitrate test. Drying of the distillation residue under reduced pressure at 1.3 Pa and 70° C. gives 28.8 g of tetrabutylammonium tetrafluoroborate. The yield is approximately quantitative. The chloride content in the ionic liquid is 118 ppm, measured as described in Example 1.

$^1$H NMR spectrum, ppm (acetonitrile-$D_3$; reference: TMS): 0.99 t ($4CH_3$); 1.38 t,q ($4CH_2$); 1.63 m ($4CH_2$); 3.11 s ($4CH_2$); $^3J_{H,H}$=7.2 Hz.

$^{11}$B NMR spectrum, ppm (acetonitrile-$D_3$; reference: $BF_3.OEt_2$-external): −1.24 s ($BF_4^-$).

$^{19}$F NMR spectrum, ppm (acetonitrile-$D_3$; reference: $CCl_3F$-internal): −150.47 s ($BF_4^-$).

EXAMPLE 6

Synthesis of 1-butyl-3-methylimidazolium trifluoromethanesulfonate

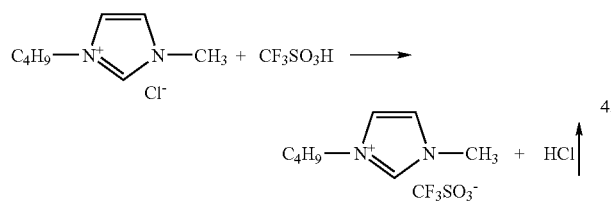

Analogously to Example 1, 174.7 g (1.0 mol) of 1-butyl-3-methylimidazolium chloride are reacted with 153.2 g (1.0 mol) of 98% $CF_3SO_3H$. 200 ml of 1,4-dioxane are subsequently added, and 200 ml of HCl-containing water/dioxane azeotrope are distilled off at atmospheric pressure (85-101° C.). The azeotropic distillation is carried out a further twice (addition of 150 ml of dioxane in each case and removal of 150 ml of HCl-containing water/dioxane mixture by distillation in each case (95-101° C.)).

Drying of the distillation residue under reduced pressure at 1.3 Pa and 70° C. gives 1-butyl-3-methylimidazolium trifluoromethanesulfonate as liquid. The yield is approximately quantitative. The chloride content in the ionic liquid is 9 ppm, measured as described in Example 1.

$^1$H NMR spectrum, ppm (acetonitrile-$D_3$; reference: TMS): 0.91 t ($CH_3$); 1.31 m ($CH_2$); 1.82 m ($CH_2$); 3.87 s ($CH_3$); 4.17 t ($CH_2$); 7.46 d,d (CH); 7.52 d,d (CH); 8.74 br.s (CH); $^3J_{H,H}$=7.3 Hz; $J_{H,H}$=1.8 Hz.

$^{19}$F NMR spectrum, ppm (acetonitrile-$D_3$; reference: $CCl_3F$-internal): −78.10 q,q ($CF_3SO_3^-$).

EXAMPLE 7

Synthesis of 1-hexyl-3-methylimidazolium hexafluorosilicate

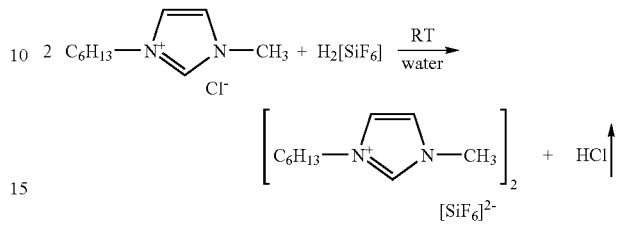

Analogously to Example 1, 150.1 g (0.740 mol) of 1-hexyl-3-methylimidazolium chloride are reacted with 218.8 g of approx. 25% aqueous $H_2SiF_6$ (approx. 3% excess). 600 ml of 1,4-dioxane are subsequently added, and 695 ml of HCl-containing water/dioxane azeotrope are distilled off at atmospheric pressure (85° C.). A further 310 ml of dioxane are then added, and 380 ml of HCl-containing water/dioxane mixture are distilled off at atmospheric pressure (85-101° C.). A silver nitrate test cannot be carried out owing to the low solubility of silver(I) hexafluorosilicate. An azeotropic distillation was then carried out a further three times with 100 ml of dioxane each time. Drying of the distillation residue under reduced pressure at 1.3 Pa and 70° C. gives 171.1 g of 1-hexyl-3-methylimidazolium hexafluorosilicate as highly viscous product, corresponding to a yield of 97.0%.

$^1$H NMR spectrum, ppm (acetonitrile-$D_3$; reference: TMS): 0.84 m ($CH_3$); 1.27 m ($3CH_2$); 1.83 m ($CH_2$); 3.91 s ($CH_3$); 4.22 t ($CH_2$); 7.60 d,d (CH); 7.64 d,d (CH); 9.73 m (CH); $^3J_{H,H}$=7.3 Hz; $J_{H,H}$=1.7 Hz.

$^{19}$F NMR spectrum, ppm (acetonitrile-$D_3$; reference: $CCl_3F$-internal): −136.27 br.s ($SiF_6^{2-}$).

EXAMPLE 8

Synthesis of 1-butyl-3-methylimidazolium hexafluorotitanate

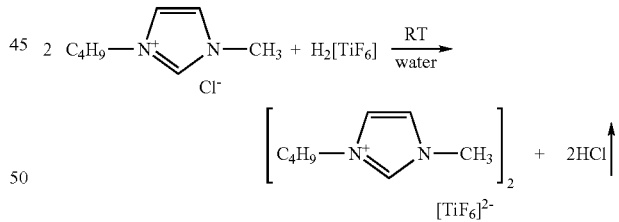

Analogously to Example 1, 76.3 g (0.437 mol) of 1-butyl-3-methylimidazolium chloride are reacted with 61.5 g of approx. 60% aqueous $H_2TiF_6$. 100 ml of 1,4-dioxane are subsequently added, and 121 ml of HCl-containing water/dioxane azeotrope are distilled off at atmospheric pressure (85° C.). A further 100 ml of dioxane are then added, and 104 ml of HCl-containing water/dioxane mixture are distilled off at atmospheric pressure (85-101° C.). After three further azeotropic distillations with 100 ml of 1,4-dioxane each time and drying of the distillation residue under reduced pressure at 1.3 Pa and 60° C., 1-butyl-3-methylimidazolium hexafluorotitanate is obtained as a highly viscous product. The yield is approximately quantitative.

$^1$H NMR spectrum, ppm (acetonitrile-$D_3$; reference: TMS): 0.88 t ($CH_3$); 1.28 m ($CH_2$); 1.77 m ($CH_2$); 3.86 s (CH$_3$); 4.17 t (CH$_2$); 7.42 d,d (CH); 7.43 d,d (CH); 8.54 m (CH); $^3J_{H,H}$=7.3 Hz; $J_{H,H}$=1.8 Hz.

EXAMPLE 9

Synthesis of 1-butyl-3-methylimidazolium tosylate

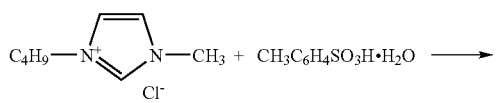

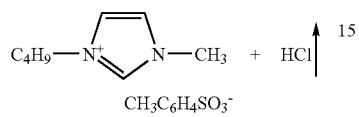

86.3 g (0.494 mol) of 1-butyl-3-methylimidazolium chloride and 94.9 g (0.499 mol) of toluenesulfonic acid monohydrate are dissolved in 50 ml of 1,4-dioxane at RT. 58 ml of HCl-containing water/dioxane azeotrope are subsequently distilled off at atmospheric pressure (85-101° C). After 22 additional azeotropic distillations with 200 ml of dioxane each time and drying of the distillation residue under reduced pressure at 1.3 Pa and 80° C., 1-butyl-3-methylimidazolium tosylate is obtained. The yield is approximately quantitative.

$^1$H NMR spectrum, ppm (acetonitrile-D$_3$; reference: TMS): 0.88 t (CH$_3$); 1.26 m (CH$_2$); 1.74 m (CH$_2$); 2.34 s (CH$_3$); 3.83 s (CH$_3$); 4.11 t (CH$_2$); 7.18 d,m (2 CH, A); 7.43 d,d (CH); 7.46 d,d (CH); 7.64 d,m (2 CH, B); 9.01 m (CH); $^3J_{H,H}$=7.3 Hz; $J_{A,B}$=8 Hz; $J_{H,H}$=1.8 Hz.

EXAMPLE 10

Synthesis of 1-butyl-3-methylimidazolium methylsulfonate

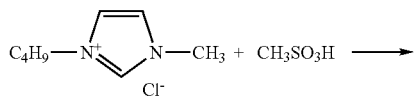

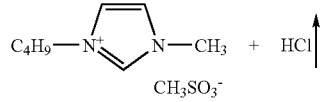

Analogously to Example 1, 26.5 g (0.152 mol) of 1-butyl-3-methylimidazolium chloride are reacted with 21.4 g of approx. 70% aqueous methanesulfonic acid, CH$_3$SO$_3$H. 100 ml of 1,4-dioxane are subsequently added, and 107 ml of HCl-containing water/dioxane azeotrope are distilled off at atmospheric pressure (85-101° C.). After 18 additional azeotropic distillations with 100 ml of 1,4-dioxane each time and drying of the distillation residue under reduced pressure at 1.3 Pa and 80° C., 1-butyl-3-methylimidazolium methylsulfonate is obtained. The yield is approximately quantitative.

$^1$H NMR spectrum, ppm (acetonitrile-D$_3$; reference: TMS): 0.89 t (CH$_3$); 1.28 m (CH$_2$); 1.80 m (CH$_2$); 2.60 s (CH$_3$); 3.89 s (CH$_3$); 4.20 t (CH$_2$); 7.57 d,d (CH); 7.61 d,d (CH); 9.34 m (CH); $^3J_{H,H}$=7.3 Hz; $J_{H,H}$=1.8 Hz.

EXAMPLE 11

Synthesis of 1-butyl-3-methylimidazolium hydrosulfate

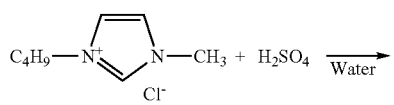

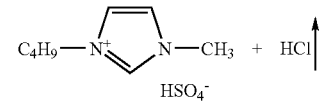

Analogously to Example 1, 67.6 g (0.387 mol) of 1-butyl-3-methylimidazolium chloride are reacted with 43.0 g of approx. 90% aqueous sulfuric acid, H$_2$SO$_4$. 80 ml of 1,4-dioxane are subsequently added, and 84 ml of HCl-containing water/dioxane azeotrope are distilled off at atmospheric pressure (85-101° C.). After four additional azeotropic distillations with 80 ml of 1,4-dioxane each time and drying of the distillation residue under reduced pressure at 1.3 Pa and 80° C., 1-butyl-3-methylimidazolium hydrosulfate is obtained. The yield is approximately quantitative.

$^1$H NMR spectrum, ppm (acetonitrile-D$_3$; reference: TMS): 0.86 t (CH$_3$); 1.26 m (CH$_2$); 1.77 m (CH$_2$); 3.86 s (CH$_3$); 4.16 t (CH$_2$); 7.45 d,d (CH); 7.47 d,d (CH); 8.92 m (CH); 10.95 br.s (SO$_4$H); $^3J_{H,H}$=7.3 Hz; $J_{H,H}$=1.8 Hz.

EXAMPLE 12

Synthesis of 1-butyl-3-methylimidazolium trifluoroacetate

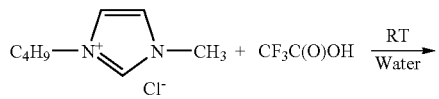

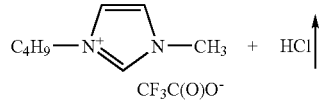

Analogously to Example 1, 23.0 g (0.132 mol) of 1-butyl-3-methylimidazolium chloride are reacted with 28.0 g of approx. 80% aqueous trifluoroacetic acid, CF$_3$C(O)OH (50% excess). 100 ml of 1,4-dioxane are subsequently added, and 112 ml of HCl- and CF$_3$C(O)OH-containing water/dioxane azeotrope are distilled off at atmospheric pressure (85-101° C.). After four further azeotropic distillations with 100 ml of 1,4-dioxane each time, a further 19 g of approx. 80% aqueous trifluoroacetic acid are added to the residue. 100 ml of 1,4-dioxane are subsequently added, and 105 ml of HCl- and CF$_3$C(O)OH-containing water/dioxane azeotrope are distilled off at atmospheric pressure. After three further azeotropic distillations with 100 ml of 1,4-dioxane each time and drying of the distillation residue under reduced pressure at 1.3 Pa and 70° C., 1-butyl-3-methylimidazolium trifluoroacetate is obtained. The yield is approximately quantitative.

$^1$H NMR spectrum, ppm (acetonitrile-D$_3$; reference: TMS): 0.92 t (CH$_3$); 1.32 m (CH$_2$); 1.81 m (CH$_2$); 3.85 s (CH$_3$); 4.15 t (CH$_2$); 7.38 m (CH); 7.42 m (CH); 8.61 m (CH); $^3J_{H,H}$=7.4 Hz.

$^{19}$F NMR spectrum, ppm (acetonitrile-D$_3$; reference: CCl$_3$F-internal): 75.60 s (CF$_3$C(O)O$^-$).

The invention claimed is:

1. A process for preparation of an onium salt having a low chloride content, said process comprising:

reacting an onium chloride with an acid resulting in formation of hydrochloric acid, wherein the hydrochloric acid formed is removed by azeotropic distillation by coordination to 1,4-dioxane which forms an azeotropic mixture with water;

wherein said onium chloride is of formulas (1), (2), (3), (4), or (5):

[NR$_4$]$^+$Cl$^-$ (1),

[PR$_4$]$^+$Cl$^-$ (2),

[(R$^1$R$^2$N)—C(=SR$^7$)(NR$^3$R$^4$)]$^+$Cl$^-$ (3),

[C(NR$^1$R$^2$)(NR$^3$R$^4$)(NR$^5$R$^6$)]$^+$Cl$^-$ (4),

[HetN]$^+$Cl$^-$ (5), wherein

R is in each case, independently of one another,
H, wherein all substituents R are not simultaneously H,
straight-chain or branched alkyl having 1-20 C atoms,
straight-chain or branched alkenyl having 2-20 C atoms and one or more double bonds,
straight-chain or branched alkynyl having 2-20 C atoms and one or more triple bonds, or saturated, partially or fully unsaturated cycloalkyl having 3-7 C atoms, which is optionally substituted by alkyl groups having 1-6 C atoms,
where one or more R groups is optionally partially or fully substituted by halogens, or partially substituted by —NO$_2$, and wherein all four or three R cannot be fully substituted by halogens, and
where, in the R, one or two non-adjacent carbon atoms which are not in the α-position are optionally replaced by atoms and/or atom groups selected from —O—, —S—, —S(O)—, —SO$_2$— or —P(O)R'—, where R' is non-fluorinated, partially fluorinated or perfluorinated C$_1$- to C$_6$-alkyl, C$_3$- to C$_7$-cycloalkyl, or unsubstituted or substituted phenyl;

R$^1$, R$^2$, R$^3$, R$^4$, R$^5$, R$^6$, and R$^7$ are each, independently of one another,
hydrogen, where hydrogen is excluded for R$^7$,
straight-chain or branched alkyl having 1 to 20 C atoms,
straight-chain or branched alkenyl having 2-20 C atoms and one or more double bonds,
straight-chain or branched alkynyl having 2-20 C atoms and one or more triple bonds, or saturated, partially or fully unsaturated cycloalkyl having 3-7 C atoms, which is optionally substituted by alkyl groups having 1-6 C atoms,
where one or more of the substituents R$^1$, R$^2$, R$^3$, R$^4$, and R$^7$ are optionally partially or fully substituted by halogens, or partially substituted by —NO$_2$, and wherein all substituents on an N atom cannot be fully substituted by halogens, and
where, in the substituents R$^1$, R$^2$, R$^3$, and R$^4$, one or two non-adjacent carbon atoms which are not bonded directly to the heteroatom are optionally replaced by atoms and/or atom groups selected from —O—, —S—, —S(O)—, —SO$_2$— or —P(O)R'—, where R' is non-flourinated, partially flourinated, or perfluorinated C$_1$- to C$_6$-alkyl, C$_3$- to C$_7$-cycloalkyl, or unsubstituted or substituted phenyl;

HetN$^+$ is a heterocyclic cation selected from

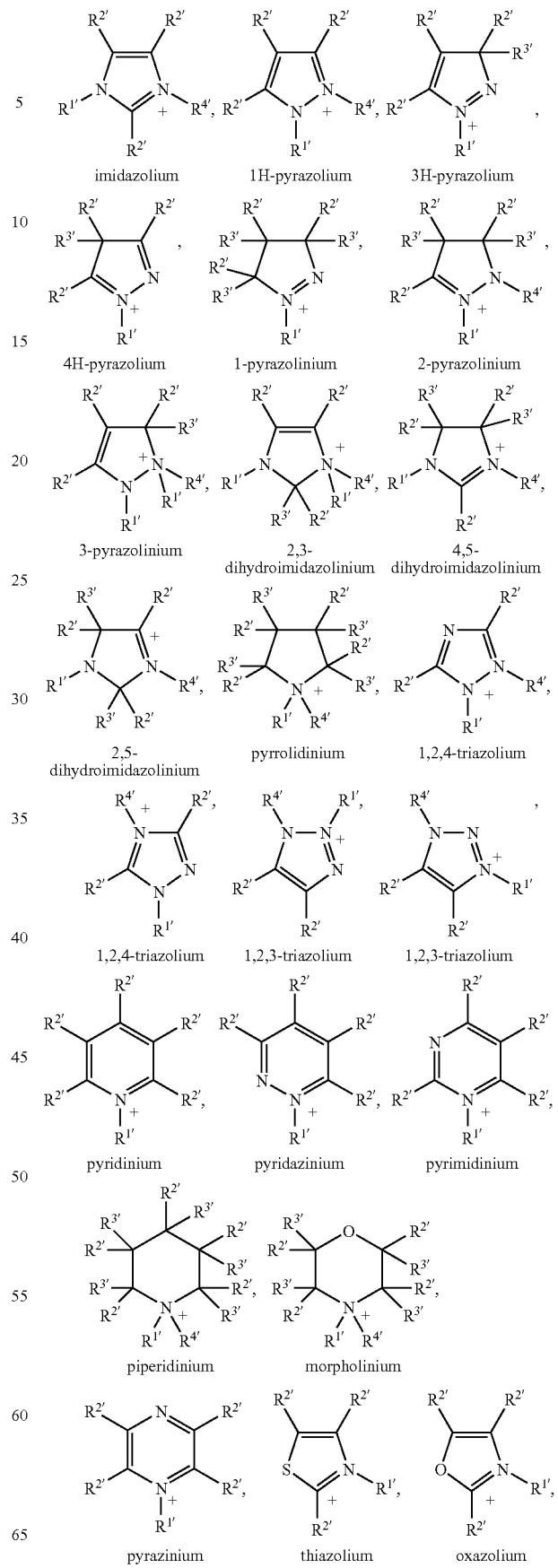

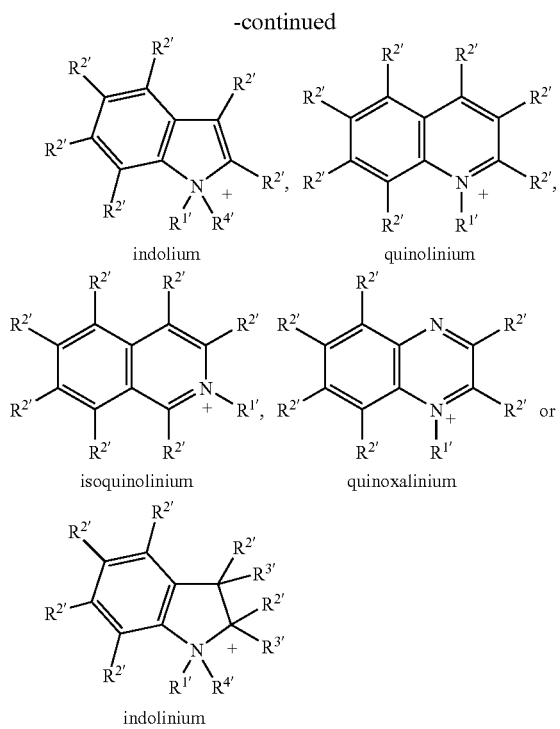

and R$^{1'}$ to R$^{4'}$ are each, independently of one another,
hydrogen,
straight-chain or branched alkyl having 1-20 C atoms,
straight-chain or branched alkenyl having 2-20 C atoms and one or more double bonds,
straight-chain or branched alkynyl having 2-20 C atoms and one or more triple bonds, saturated, partially or fully unsaturated cycloalkyl having 3-7 C atoms, which is optionally substituted by alkyl groups having 1-6 C atoms,
saturated, partially or fully unsaturated heteroaryl, or
heteroaryl-C$_1$-C$_6$-alkyl or aryl-C$_1$-C$_6$-alkyl,
where one or more of R$^{1'}$ to R$^{4'}$ are optionally partially or fully substituted by halogens, or partially substituted by —NO$_2$, and wherein R$^{1'}$ and R$^{4'}$ cannot simultaneously be fully substituted by halogens, and
where, in R$^{1'}$ to R$^{4'}$, one or two non-adjacent carbon atoms which are not bonded directly to the heteroatom are optionally replaced by atoms and/or atom groups selected from —O—, —S—, —S(O)—, —SO$_2$— or —P(O)R'—, where R' is non-fluorinated, partially fluorinated, or perfluorinated C$_1$- to C$_6$-alkyl, C$_3$- to C$_7$-cycloalkyl, or unsubstituted or substituted phenyl;
wherein in the guanidinium cation [C(NR$^1$R$^2$)(NR$^3$R$^4$)(NR$^5$R$^6$)]$^+$ of formula (4) up to four substituents are optionally connected in pairs to form mono-, bi- or polycyclic cations; and
wherein in the thiouronium cation [(R$^1$R$^2$N)—C(=SR$^7$)(NR$^3$R$^4$)]$^+$ of formula (3) up to four substituents are optionally connected in pairs to form mono-, bi- or polycyclic cations; and
with the proviso that compounds of the formulae (1) and (2) in which all of the substituents R are fully substituted by halogens or in which three of the substituents R are fully substituted by halogens are excluded.

2. A process according to claim 1, wherein said chloride is of formula (1)

[NR$_4$]$^+$Cl$^-$                  (1).

3. A process according to claim 1, wherein said chloride is of formula (2)

[PR$_4$]$^+$Cl$^-$                  (2).

4. A process according to claim 1, wherein said chloride is of formula (3)

[(R$^1$R$^2$N)—C(=SR$^7$)(NR$^3$R$^4$)]$^+$Cl$^-$        (3).

5. A process according to claim 1, wherein said chloride is of formula (4)

[C(NR$^1$R$^2$)(NR$^3$R$^4$)(NR$^5$R$^6$)]$^+$Cl$^-$        (4).

6. A process according to claim 1, wherein said chloride is of formula (5)

[HetN]$^+$Cl$^-$                  (5).

7. A process according to claim 1, wherein said acid is HBF$_4$, H$_2$SiF$_6$, H$_2$TiF$_6$, H$_2$ZrF$_6$, HSbF$_6$, HAsF$_6$, HPF$_6$, HN(CN)$_2$, HC(CN)$_3$, H$_2$SO$_4$, HNO$_3$, an alkyl- or perfluoroalkylsulfonic acid, an aromatic sulfonic acid, a perfluoroalkylcarboxylic acid, an alkyl- or perfluoroalkylphosphinic acid, an alkyl- or perfluoroalkylphosphonic acid, an aromatic phosphinic or phosphonic acid, or phosphoric acid.

8. A process according to claim 1, wherein reaction of the chloride with the acid is carried out in water.

9. A process according to claim 1, wherein said the azeotropic distillation is carried out batchwise at atmospheric pressure or under reduced pressure.

10. A process according to claim 1, wherein said azeotropic distillation is carried out semicontinuously at atmospheric pressure or under reduced pressure.

11. A process according to claim 1, wherein said the azeotropic distillation is carried out continuously at atmospheric pressure or under reduced pressure.

12. A process according to claim 1, wherein the resultant onium salt has a halide content below 500 ppm.

13. A process according to claim 1, wherein the resultant onium salt has a halide content below 100 ppm.

14. A process according to claim 1, wherein the resultant onium salt has a halide content below 20 ppm.

15. A process according to claim 1, wherein said acid is aqueous HBF$_4$, H$_2$SiF$_6$, H$_2$TiF$_6$, H$_2$SO$_4$, CF$_3$SO$_3$H, CF$_3$COOH, toluenesulfonic acid monohydrate, or CH$_3$SO$_3$H.

16. A process according to claim 12, wherein said acid is aqueous HBF$_4$, H$_2$SiF$_6$, H$_2$TiF$_6$, H$_2$SO$_4$, CF$_3$SO$_3$H, CF$_3$COOH, toluenesulfonic acid monohydrate, or CH$_3$SO$_3$H.

17. A process according to claim 3, wherein R is methyl, ethyl, isopropyl, propyl, butyl, sec-butyl, pentyl, hexyl, octyl, decyl or tetradecyl.

18. A process according to claim 4, wherein R$^1$, R$^2$, R$^3$, R$^4$, and R$^7$ are each, independently of one another, a straight-chain or branched alkyl group having 1 to 10 C atoms.

19. A process according to claim 4, wherein R$^1$, R$^2$, R$^3$, R$^4$, and R$^7$ are each, independently of one another, methyl, ethyl, n-propyl, isopropyl, n-butyl, sec-butyl, phenyl or cyclohexyl.

20. A process according to claim 5, wherein R$^1$ to R$^6$ are each, independently of one another, a straight-chain or branched alkyl group having 1 to 10 C atoms.

21. A process according to claim 5, wherein R$^1$ to R$^6$ are each, independently of one another, methyl, ethyl, n-propyl, isopropyl, n-butyl, sec-butyl, phenyl or cyclohexyl.

22. A process according to claim 6, wherein R$^{1'}$ and R$^{4'}$ are each, independently of one another, methyl, ethyl, isopropyl, propyl, butyl, sec-butyl, pentyl, hexyl, octyl, decyl, cyclohexyl, phenyl or benzyl, and R$^{2'}$ and R$^{3'}$ are each, independently of one another, hydrogen, methyl, ethyl, isopropyl, propyl, butyl, sec-butyl, cyclohexyl, phenyl or benzyl.

23. A process according to claim 6, wherein $R^{1'}$ to $R^{4'}$ are each,

H, methyl, ethyl, isopropyl, propyl, butyl, sec-butyl or tert-butyl, pentyl, 1-methylbutyl, 2-methylbutyl, 3-methylbutyl, 1,1-dimethylpropyl, 1,2-dimethylpropyl, 2,2-dimethylpropyl, 1-ethylpropyl, hexyl, heptyl, octyl, nonyl, decyl, undecyl, or dodecyl;

allyl, 2-butenyl, 3-butenyl, isobutenyl, sec-butenyl, 4-pentenyl, isopentenyl, or hexenyl;

ethynyl, 1-propynyl, 2-propynyl, 2-butynyl, 3-butynyl, 4-pentynyl, 3-pentynyl, or hexynyl;

benzyl, phenylethyl, phenylpropyl, phenylbutyl, phenylpentyl or phenylhexyl, wherein both the phenyl ring and the alkylene chain are each optionally partially or fully substituted by halogens or partially substituted by $-NO_2$;

cyclopropyl, cyclobutyl, cyclopentyl, cyclohexyl, cycloheptyl, cyclopentenyl, cyclopenta-1,3-dienyl, cyclohexenyl, cyclohexa-1,3-dienyl, cyclohexa-1,4-dienyl, phenyl, cycloheptenyl, cyclohepta-1,3-dienyl, cyclohepta-1,4-dienyl or cyclohepta-1,5-dienyl, which in each case are optionally substituted by $C_1$- to $C_6$-alkyl groups, and the cycloalkyl group or cycloalkyl group substituted by $C_1$- to $C_6$-alkyl groups are also optionally substituted by halogen atoms or $NO_2$; or $-OCH_3$, $-OCH(CH_3)_2$, $-CH_2OCH_3$, $-CH_2-CH_2-O-CH_3$, $-C_2H_4OCH(CH_3)_2$, $-C_2H_4SC_2H_5$, $-C_2H_4SCH(CH_3)_2$, $-S(O)CH_3$, $-SO_2CH_3$, $-SO_2C_6H_5$, $-SO_2C_3H_7$, $-SO_2CH(CH_3)_2$, $-SO_2CH_2CF_3$, $-CH_2SO_2CH_3$, $-O-C_4H_8-O-C_4H_9$, $-CF_3$, $-C_2F_5$, $-C_3F_7$, $-C_4F_9$, $-C(CF_3)_3$, $-CF_2SO_2CF_3$, $-C_2F_4N(C_2F_5)C_2F_5$, $-CHF_2$, $-CH_2CF_3$, $-C_2F_2H_3$, $-C_3FH_6$, $-CH_2C_3F_7$, $-CH_2C(O)OH$, $-CH_2C_6H_5$, $-C(O)C_6H_5$ or $P(O)(C_2H_5)_2$.

24. A process according to claim 1, wherein said chloride is 1-butyl-3-methylimidazolium chloride, 1-butyl-4-methylpyridinium chloride, 1-ethyl-3-methylimidazolium chloride, trihexyl(tetradecyl)phosphonium chloride, tetrabutylammonium chloride, or 1-hexyl-3-methylimidazolium chloride.

25. A process according to claim 16, wherein said chloride is 1-butyl-3-methylimidazolium chloride, 1-butyl-4-methylpyridinium chloride, 1-ethyl-3-methylimidazolium chloride, trihexyl(tetradecyl)phosphonium chloride, tetrabutylammonium chloride, or 1-hexyl-3-methylimidazolium chloride.

26. A process according to claim 1, wherein said onium salt is 1-butyl-3-methylimidazolium tetrafluoroborate, 1-butyl-4-methylpyridinium tetrafluoroborate, 1-ethyl-3-methylimidazolium tetrafluoroborate, trihexyl(tetradecyl)phosphonium tetrafluoroborate, tetrabutylammonium tetrafluoroborate, 1-butyl-3-methylimidazolium trifluoromethane-sulfonate, 1-hexyl-3-methylimidazolium hexafluorosilicate, 1-butyl-3-methylimidazolium hexafluorotitanate, 1-butyl-3-methylimidazolium tosylates, 1-butyl-3-methylimidazolium methylsulfonate, 1-butyl-3-methylimidazolium hydrosulfate, or 1-butyl-3-methylimidazolium trifluoroacetate.

27. A process according to claim 1, wherein substituents R, $R^1$ to $R^7$, and $R^{1'}$ to $R^{4'}$ of the compounds of the formulae (1) to (5) are each independently H, $C_1$- to $C_{20}$-alkyl, or saturated or unsaturated $C_3$- to $C_7$-cycloalkyl groups optionally substituted by $C_1$- to $C_6$-alkyl groups.

28. A process according to claim 27, wherein substituents R, $R^1$ to $R^7$, and $R^{1'}$ to $R^{4'}$ of the compounds of the formulae (1) to (5) are each independently H, $C_1$- to $C_{14}$-alkyl, or phenyl.

29. A process according to claim 1, wherein said onium chloride is of formula (1) or formula (2), and R is methyl, ethyl, isopropyl, propyl, butyl, sec-butyl, pentyl, hexyl, octyl, decyl, or tetradecyl.

30. A process according to claim 1, wherein said onium chloride is of formula (4) and the guanidinium cation of formula (4) is selected from:

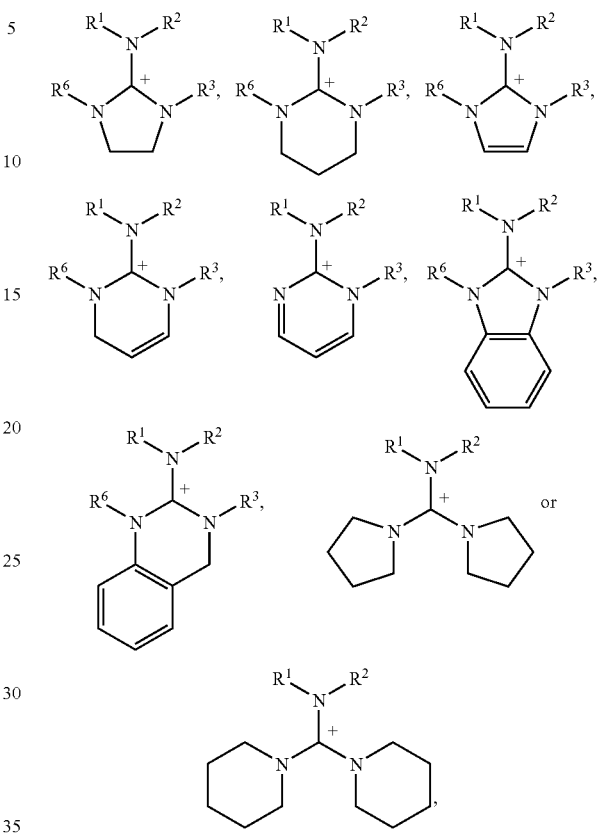

wherein
the carbocycles or heterocycles of the guanidinium cations are optionally substituted by $C_1$- to $C_6$-alkyl, $C_1$- to $C_6$-alkenyl, $NO_2$, F, Cl, Br, I, OH, $C_1$-$C_6$-alkoxy, $SCF_3$, $SO_2CF_3$, COOH, $SO_2NR''$, $SO_2X'$ or $SO_3H$, X' is F, Cl or Br, and R" is a non-, partially or perfluorinated $C_1$- to $C_6$-alkyl or $C_3$- to $C_7$-cycloalkyl.

31. A process according to claim 1, wherein said onium chloride is of formula (3) and the thiouronium cation of formula (3) is selected from:

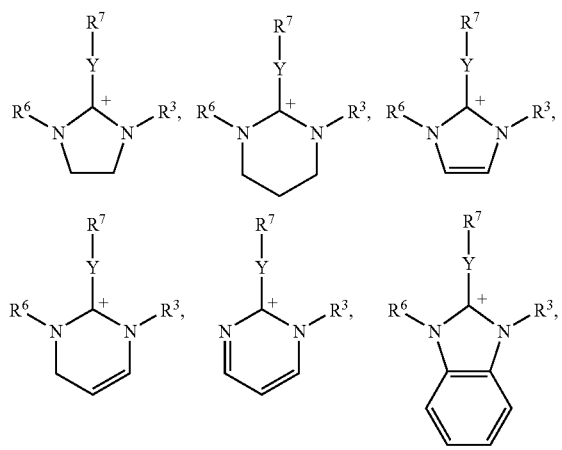

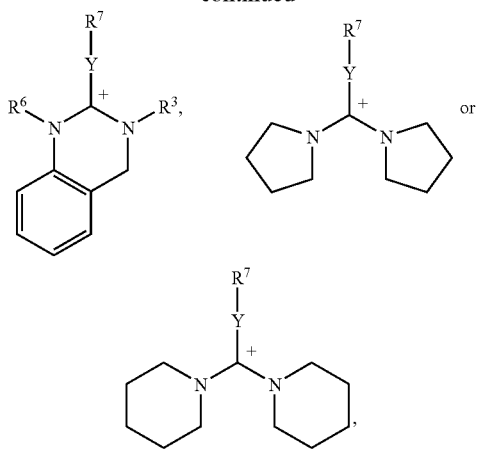

wherein
Y is S,
the carbocycles or heterocycles of the guanidinium cations are optionally substituted by $C_1$- to $C_6$-alkyl, $C_1$- to $C_6$-alkenyl, $NO_2$, F, Cl, Br, I, OH, $C_1$-$C_6$-alkoxy, $SCF_3$, $SO_2CF_3$, COOH, $SO_2NR''$, $SO_2X'$ or $SO_3H$,
X' is F, Cl or Br, and
R'' is a non-, partially or perfluorinated $C_1$- to $C_6$-alkyl or $C_3$- to $C_7$-cycloalkyl.

32. A process according to claim 1, wherein
R is methyl, ethyl, isopropyl, propyl, butyl, sec-butyl, pentyl, hexyl, octyl, decyl, or tetradecyl;
$R^1$ to $R^7$ are each, independently of one another, a straight-chain or branched alkyl group having 1 to 10 C atoms;
$R^{1'}$ and $R^{4'}$ are each, independently of one another, methyl, ethyl, isopropyl, propyl, butyl, sec-butyl, pentyl, hexyl, octyl, decyl, cyclohexyl, phenyl or benzyl; and
$R^{2'}$ or $R^{3'}$ are each, independently of one another, hydrogen, methyl, ethyl, isopropyl, propyl, butyl, sec-butyl, cyclohexyl, phenyl or benzyl.

* * * * *

UNITED STATES PATENT AND TRADEMARK OFFICE
CERTIFICATE OF CORRECTION

PATENT NO.         : 7,692,007 B2
APPLICATION NO.    : 11/632313
DATED              : April 6, 2010
INVENTOR(S)        : Nikolai Ignatyev et al.

It is certified that error appears in the above-identified patent and that said Letters Patent is hereby corrected as shown below:

Column 21, line 31 reads: "and $R^{1,}$ to $R^{4,}$ are each independently of one another,"

Should read: -- and $R^{1'}$ to $R^{4'}$ are each independently of one another, --

Column 21, line 43 reads: "where one or more of $R^{1,}$ to $R^{4,}$ are optionally partially or"

Should read: -- where one or more of $R^{1'}$ to $R^{4'}$ are optionally partially or --

Column 21, line 45 reads: "-$NO_2$, and wherein $R^{1,}$ to $R^{4,}$ cannot simultaneously"

Should read: -- -$NO_2$, and wherein $R^{1'}$ to $R^{4'}$ cannot simultaneously --

Column 21, line 47 reads: "where, in $R^{1,}$ to $R^{4,}$, one or two non-adjacent carbon atoms"

Should read: -- where, in $R^{1'}$ to $R^{4'}$, one or two non-adjacent carbon atoms --

Signed and Sealed this

Sixteenth Day of November, 2010

David J. Kappos
*Director of the United States Patent and Trademark Office*